United States Patent
Euzen et al.

(12) 
(10) Patent No.: US 7,262,333 B2
(45) Date of Patent: Aug. 28, 2007

(54) PROCESS FOR THE PRODUCTION OF PHENYLALKANES THAT USE A CATALYST BASED ON SILICATED ALUMINA

(75) Inventors: Patrick Euzen, Paris (FR); Emmanuelle Guillon, Saint Genis Laval (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 371 days.

(21) Appl. No.: 10/981,740

(22) Filed: Nov. 5, 2004

(65) Prior Publication Data
US 2005/0177017 A1 Aug. 11, 2005

(30) Foreign Application Priority Data
Nov. 5, 2003 (FR) .................. 03 13083

(51) Int. Cl.
*C07C 2/68* (2006.01)
(52) U.S. Cl. .................................... 585/455
(58) Field of Classification Search ............... 585/455
See application file for complete search history.

(56) References Cited

U.S. PATENT DOCUMENTS 5,302,732 A  4/1994 Steigleder et al.
6,166,281 A  12/2000 Anantaneni
6,429,345 B1  8/2002 Joly et al.

FOREIGN PATENT DOCUMENTS

EP  0615968 A  9/1994
FR  2697246 A  4/1994

*Primary Examiner*—Thuan Dinh Dang
(74) *Attorney, Agent, or Firm*—Millen, White, Zelano & Branigan, P.C.

(57) ABSTRACT

The invention relates to a process for the production of at least one compound that is selected from among the 2-, 3-, 4-, 5-, and 6-phenylalkanes by alkylation of an aromatic compound by means of at least one olefin that comprises at least 9 carbon atoms per molecule, in the presence of a catalyst that comprises at least one non-zeolitic substrate with a silicated alumina base that contains an amount of more than 6% by weight and less than or equal to 50% by weight of silica ($SiO_2$) and that exhibits particular characteristics, whereby said process is carried out at a temperature of between 30 and 400° C., a pressure of between 0.1 and 10 MPa, an hourly volumetric flow rate of 0.50 to 200 h−1, and an aromatic compound/olefin molar ratio of between 1:1 and 50:1.

22 Claims, No Drawings

PROCESS FOR THE PRODUCTION OF PHENYLALKANES THAT USE A CATALYST BASED ON SILICATED ALUMINA

TECHNICAL FIELD

This invention relates to the field of the processes of production of phenylalkanes by alkylation of aromatic compounds by means of at least one olefin that comprises at least 9 carbon atoms per molecule. More particularly, for example, a hydrocarbon fraction that comprises at least one olefin that has 9 to 16 carbon atoms or 10 to 14 carbon atoms per molecule or, for example, a hydrocarbon fraction that comprises at least one olefin that has 14 to 20 carbon atoms, in the presence of at least one catalyst that is supported on a non-zeolitic substrate that comprises a particular silicated alumina, will be used.

PRIOR ART

The phenylalkanes that are obtained according to the invention constitute compounds for the formulation, after sulfonation, of biodegradable detergents.

Currently, the bases for biodegradable detergents rely extensively on linear alkylbenzenes. The production of this type of compound increases regularly. One of the primary properties sought for these compounds, after the sulfonation stage, is, in addition to their detergent power, their biodegradability. To ensure maximum biodegradability, the alkyl group should be linear and long, and the distance between the sulfonate group and the terminal carbon of the linear chain should be at a maximum. The most advantageous agents for alkylation of benzene consist of C9-C16 linear olefins, and preferably C10-C14 linear olefins.

The linear alkylbenzenes that are obtained by alkylation of aromatic compounds, preferably by alkylation of benzene by means of (a) linear olefin(s) are prepared today by two major processes. During the alkylation stage, the first process uses benzene or aromatic compounds, or hydrofluoric acid as an acid catalyst. The second uses a Friedel-Craft-type catalyst, in particular with an $AlCl_3$ base. These two processes lead to the formation of 2-, 3-, 4-, 5- and 6-phenylalkanes. The primary drawback of these processes is linked to environmental constraints. The first process that is based on the use of hydrofluoric acid poses severe safety problems, on the one hand, and waste treatment, on the other hand. The second process poses the standard problem of processes that use Friedel-Craft catalysts, in this case the problem of wastes. Actually, for this type of process, it is necessary to neutralize the effluents by a basic solution at the outlet of the reactor. Added to these various drawbacks for the two processes are the difficulties linked to the separation of the catalyst from the products of the reaction.

These various constraints explain the advantage of developing a process for alkylation of aromatic compounds by olefins, in particular the linear olefins, in the presence of a solid catalyst.

The prior art notes the use of various types of catalysts such as crystallized catalysts that have geometric selectivity properties such as the U.S. Pat. No. 4,301,317 zeolites, clays, amorphous catalysts such as the silica-aluminas or the catalysts based on supported heteropolyanions.

U.S. Pat. No. 5,344,997, U.S. Pat. No. 5,245,094 and U.S. Pat. No. 5,302,732 describe the use of amorphous silica-aluminas, with or without the presence of fluorine and/or with very low sodium contents with $SiO_2$—$Al_2O_3$ compositions in the range of 1:1 to 9:1, and preferably in the range of 65:35 to 85:15 and in particular 75:25. The solids that are disclosed are therefore for the most part silicic. The selectivity of the products of the reaction is described as increasing with the silica content.

We discovered that the use of catalysts that comprise a particular silicated alumina (composition for the most part of alumina), by alkylation of aromatic compounds by means of olefin(s) as defined above, made it possible to obtain higher catalytic performance levels than those of the catalysts that are described in the prior art. These new catalysts are at the same time in particular very active, very selective and very resistant to deactivation.

DESCRIPTION

The invention relates to a process for the production of at least one compound that is selected from among the 2-, 3-, 4-, 5-, and 6-phenylalkanes by alkylation of an aromatic compound, preferably by alkylation of benzene by means of at least one olefin that contains at least 9 carbon atoms per molecule, in the presence of a catalyst that comprises at least one non-zeolitic substrate that is based on a particular silicated alumina; said alkylation reaction is carried out under a pressure of about 0.1 to 10 MPa, a temperature of about 30 to 400° C., an hourly volumetric flow rate of about 0.5 to 200 $h^{-1}$ and a molar ratio of the aromatic compound to all the olefin(s) contained in the feedstock of about 1:1 to 50:1. The invention relates most particularly to the alkylation of an aromatic compound by means of a linear olefin for the purpose of producing linear phenylalkanes.

Within the framework of this invention, the hydrocarbon feedstock that is used to carry out the alkylation of the benzene core can contain, in addition to at least one olefin as defined above, one or more paraffins, one or more other aromatic compound(s), one or more polyolefinic compound (s), for example diolefinic compound(s), one or more mono- and/or poly-unsaturated non-linear olefin(s) and optionally hydrogen. These fractions can also contain one or more alpha-olefin(s) in a very variable amount from the trace state up to very large amounts, and even in the majority for the most part relative to said feedstock. The olefins can be linear or branched olefins. The hydrocarbon feedstock preferably comprises a majority of paraffins.

The process according to this invention makes it possible to produce, preferably simultaneously, at least one compound that is selected from among the 2-, 3-, 4-, 5-, and 6-phenylalkanes. In the case where the feedstock comprises linear olefins, the process according to the invention makes it possible to produce linear phenylalkanes for the most part. In the case where the feedstock comprises branched olefins, the process according to the invention makes it possible to produce branched phenylalkanes for the most part.

The catalyst that is used in this invention comprises at least one silicated alumina.

In the following specification of the invention, the term "alumine silicaée" (in English: "silicated alumina") refers to silica aluminas with compositions for the most part of alumina, i.e., that contain a percentage of alumina that is generally higher than 50%. This delimitation can be illustrated, without it being limiting, by the following articles: "Silicated Aluminas Prepared from TEOS: Catalysts for Isomerization of Butenes," Ind. Eng. Chem. Fundam. 19886, 25, 337-343. B. Nilsen, J. Onuferko and B. C. Gates and "FT-IR Characterization of Silicated Aluminas, Active Olefin Skeletal Isomerization Catalysts," Catalysis Today, 1997, 335-352, E. Finocchio, G. Busca, S. Rossini, U. Cornaro, V. Piccoli, R. Miglio. The literature teaches the basic differences in terms of acidity between the silicated aluminas and the other silica-aluminas. In particular, we can cite: "FT-IR Studies on Light Olefin Skeletal Isomerization Catalysis," J. Cat. 179, 581-591, 1998. M. Trombetta, G. Busca, S. Rossini, U. Cornaro, A. Guercio, R. Catani, and R. Willey. It may also be advantageous to refer to the article by M. Sato, $3^{rd}$ Int. Cong. of Cat. North Holland, Amsterdam, showing the development of the acidity based on the increasing silica composition and demonstrating the increase in Bronsted acidity up to an optimum 50 to 60% of silica.

In addition, this distribution line also takes into account the fact that the synthesis modes are, most of the time, basically different between the compositions for the most part of alumina and those that are for the most part of silica.

The applicant discovered in particular that, preferably and surprisingly, the interaction between the fluorine and the alumina that are present in the silicated alumina creates a synergy effect that does not exist between fluorine and silica-alumina.

In addition, this catalyst that is shaped, for example, in the form of balls or extrudates exhibits good mechanical resistance.

DETAILED DESCRIPTION OF THE INVENTION

Characterization Techniques

In the following specification of the invention, specific surface area is defined as the B.E.T. specific surface area that is determined by nitrogen adsorption according to the ASTM D 3663-78 standard established from the BRUNAUER-EMMETT-TELLER method described in the periodical "The Journal of American Society," 60, 309, (1938).

In the following specification of the invention, mercury volume of the substrates and catalysts is defined as the volume that is measured by mercury porosimeter intrusion according to the ASTM D4284-83 standard at a maximum pressure of 4000 bar, using a surface tension of 484 dyne/cm and a contact angle of the amorphous silicated alumina substrates of 140°. The mean mercury diameter is defined as being a diameter such that all the pores of a size smaller than this diameter constitute 50% of the pore volume ($V_{HG}$), in an interval encompassed between 36 Å and 1000 Å. One of the reasons for which it is preferable to use the substrate as a base to define the pore distribution resides in the fact that the contact angle of the mercury varies after impregnation of the metals based on the nature and the type of metals. The wetting angle was assumed to be equal to 140° by following the recommendations of the work "Techniques de l'ingénieur, traité analyse et caractérisation [Engineering Techniques, Analytical Treatise and Characterization], pp. 1050-5, written by Jean Charpin and Bernard Rasneur."

To obtain better precision, the value of the mercury volume in ml/g provided in the following text corresponds to the value of the total mercury volume in ml/g that is measured on the sample less the value of the mercury volume in ml/g measured on the same sample for a pressure that corresponds to 30 psi (about 2 bar). The mean mercury diameter is also defined as being a diameter such that all the pores of a size less than this diameter constitute 50% of the total mercury pore volume.

So as to better characterize the pore distribution, the following pore distribution criteria in terms of mercury are finally defined: volume V1 corresponds to the volume that is contained in the pores whose diameter is less than the mean diameter minus 30 Å. Volume V2 corresponds to the volume that is contained in the pores with a diameter that is greater than or equal to the mean diameter minus 30 Å and less than the mean diameter plus 30 Å. Volume V3 corresponds to the volume that is contained in the pores with a diameter that is greater than or equal to the mean diameter plus 30 Å. Volume V4 corresponds to the volume that is contained in the pores whose diameter is less than the mean diameter minus 15 Å. Volume V5 corresponds to the volume that is contained in the pores with a diameter that is greater than or equal to the mean diameter minus 15 Å and less than the mean diameter plus 15 Å. Volume V6 corresponds to the volume that is contained in the pores with a diameter that is greater than or equal to the mean diameter plus 15 Å.

The pore distribution that is measured by nitrogen adsorption was determined by the Barrett-Joyner-Halenda (BJH) model. The nitrogen adsorption-desorption isotherm according to the BJH model is described in the periodical "The Journal of American Society," 73, 373, (1951) written by E. P. Barrett, L. G. Joyner and P. P. Halenda. In the following specification of the invention, nitrogen adsorption volume is defined as the volume that is measured for $P/P_o=0.99$, pressure for which it is assumed that nitrogen filled all the pores. The mean nitrogen desorption diameter is defined as being a diameter such that all of the pores that are smaller than this diameter constitute 50% of the pore volume ($V_p$) measured on the desorption branch of the nitrogen isotherm.

Adsorption surface area means the surface area that is measured on the branch of the adsorption isotherm. Reference will be made to, for example, the article by A. Lecioux "Mémoires Société Royale des Sciences de Liège, $6^{ème}$ série [$6^{th}$ Series], Tome I [Volume 1], fasc. 4 [Section 4], pp. 169-209 (1971)."

The sodium content was measured by atomic absorption spectrometry.

X diffraction is a technique that can be used to characterize the substrates and catalysts according to the invention. In the following specification, the analysis of x rays is carried out on powder with a Philips PW 1830 diffractometer that operates in reflection and is equipped with a rear monochromator by using CoKalpha radiation ($\lambda K_{\alpha 1}=1.7890$ Å, $\lambda 1 K_{\alpha 2}=1.793$ Å, intensity ratio $K_{\alpha 1}/K_{\alpha 2}=0.5$). For the X diffraction diagram of the gamma-alumina, reference will be made to the ICDD data base, form 10-0425. In particular, the two most intense peaks are located at a position that corresponds to one d encompassed between 1.39 and 1.40 Å and one d encompassed between 1.97 Å to 2.00 Å. d is called the inter-reticular distance that is derived from the angular position by using Bragg's equation ($2d_{(hkl)}*\sin(\theta)=\eta*\lambda$). Gamma-alumina is defined in the text below, i.a., as, for example, an alumina contained in the group that consists of cubic gamma-aluminas, pseudo-cubic gamma-aluminas, tetragonal gamma-aluminas, poorly or slightly crystallized gamma-aluminas, large-surface gamma-aluminas, small-surface gamma-aluminas, gamma-aluminas that are obtained from coarse boehmite, gamma-aluminas that are obtained from crystallized boehmite, gamma-aluminas that are obtained from boehmite that is slightly or poorly crystallized, gamma-aluminas that are obtained from a mixture of crystallized boehmite and an amorphous gel, gamma-aluminas that are obtained from an amorphous gel, and gamma-aluminas evolving toward delta. For the positions of diffraction peaks of eta, delta and theta aluminas, it is possible to refer to the article by B. C. Lippens and J. J. Steggerda in Physical and Chemical Aspects of Adsorbents and Catalysts, E. G. Linsen (Ed.), Academic Press, London. 1970, pp. 171-211.

For the substrates and catalysts according to the invention, the X diffraction diagram demonstrates a wide peak that is characteristic of the presence of amorphous silica.

Furthermore, in the entire text that follows, the alumina compound can contain an amorphous fraction that is difficult to detect by the DRX techniques. It will therefore be understood below that the alumina compounds that are used or described in the text can contain an amorphous or poorly crystallized fraction.

The substrates and catalysts according to the invention have been analyzed by NMR MAS of the solid of $^{27}$Al on a spectrometer of the Brücker Company such as MSL 400, with a 4 mm probe. The speed of rotation of the samples is on the order of 11 kHz. Potentially, the NMR of the aluminum makes it possible to distinguish three types of aluminum whose chemical displacements are presented below:

Between 100 and 40 ppm, tetra-coordinated-type aluminum, denoted as $Al_{IV}$,

Between 40 and 20 ppm, penta-coordinated-type aluminum, denoted as $Al_V$,

Between 20 and −100 ppm, hexa-coordinated-type aluminum, denoted as $Al_{VI}$.

The aluminum atom is a quadripolar core. Under certain analysis conditions (weak radiofrequency fields: 30 kHz, low-impulse angle: π/2 and water-saturated sample), the NMR technique of magic angle rotation (MAS) is a quantitative technique. The decomposition of the NMR MAS spectra makes it possible to gain access directly to the amount of different radicals. The spectrum is locked in chemical displacement relative to a 1 M solution of aluminum nitrate. The aluminum signal is at zero ppm. We chose to integrate the signals between 100 and 20 ppm for the $Al_{IV}$ and $Al_V$, which corresponds to area 1, and between 20 and −100 ppm for $Al_{VI}$, which corresponds to area 2. In the following specification of the invention, proportion of octahedral $Al_{VI}$ is defined as the following ratio: area 2/(area 1+area 2).

A method of characterization of the substrates and catalysts according to the invention that can be used is transmission electronic microscopy (TEM). For this purpose, an electronic microscope (such as Jeol 2010 or Philips Tecnai 20F, optionally with scanning) that is equipped with an energy dispersion spectrometer (EDS) for x-ray analysis (for example a Tracor or an Edax) is used. The EDS detector should make possible the detection of light elements. The combination of these two tools, TEM and EDS, makes it possible to combine the imagery and the local chemical analysis with a good spatial resolution.

For this type of analysis, the samples are finely ground in the dry state in a mortar; the powder is then included in the resin to produce ultrafine fractions with a thickness of about 70 nm. These fractions are collected on Cu grids that are covered by an amorphous carbon film with holes used as a substrate. They are then introduced into the microscope for observation and analysis under secondary vacuum. By imagery, the sample zones are then easily distinguished from the resin zones. A certain number of analyses, 10 at a minimum, preferably between 15 and 30, are then initiated on different zones of the industrial sample. The size of the electronic beam for the analysis of the zones (approximately determining the size of the analyzed zones) is 50 nm of diameter at a maximum, preferably 20 nm, even more preferably 10, 5, 2 or 1 nm of diameter. In the scanned mode, the analyzed zone will be based on the size of the scanned zone and no longer on the size of the beam, which is generally reduced.

The semi-quantitative treatment of X spectra collected with the help of the EDS spectrometer makes it possible to obtain the relative concentration of Al and Si (in % atomic) and the Si/Al ratio for each of the analyzed zones. It is then possible to calculate the $Si/Al_m$ mean and the standard deviation σ of this set of measurements. In the non-limiting examples of the following specification of the invention, the 50 nm probe is the probe that is used to characterize the substrates and catalysts according to the invention, unless otherwise indicated.

The packing density (DRT) is measured in the manner that is described in the work "Applied Heterogeneous Catalysis" by J. F. Le Page, J. Cosyns, P. Courty, E. Freund, J.-P. Franck, Y. Jacquin, B. Juguin, C. Marcilly, G. Martino, J. Miguel, R. Montarnal, A. Sugier, H. Van Landeghem, Technip. Paris, 1987. A graduated cylinder with acceptable dimensions is filled by successive additions, and between each addition, the catalyst is packed by shaking the cylinder until a constant volume is achieved. This measurement is generally carried out on 1000 cm$^3$ of catalyst packed into a cylinder whose height to diameter ratio is close to 5:1. This measurement can preferably be carried out on automated devices such as Autotap® that is marketed by Quantachrome®.

The acidity of the matrix is measured by infra-red (IR) spectrometry. The IR spectra are recorded on a Nicolet interferometer such as Nexus-670 under a resolution of 4 cm$^{-1}$ with a Happ-Genzel-type apodization. The sample (20 mg) is pressed in the form of a self-supported pellet and placed in an in-situ analysis cell (25° C. to 550° C., furnace offset from the IR beam, secondary vacuum of 10$^{-6}$ mbar). The diameter of the pellet is 16 mm.

The sample is pretreated in the following way to eliminate the physisorbed water and to dehydroxylate partially the surface of the catalyst to have a representative image of the acidity of the catalyst in use:

increase in temperature from 25° C. to 300° C. in 3 hours, stage of 10 hours at 300° C., drop in temperature from 300° C. to 25° C. in 3 hours.

The basic probe (pyridine) is then adsorbed with saturating pressure at 25° C. and then thermo-desorbed according to the following stages:

25° C. for 2 hours under secondary vacuum

100° C. for 1 hour under secondary vacuum

200° C. for 1 hour under secondary vacuum

300° C. for 1 hour under secondary vacuum.

A spectrum is recorded at 25° C. at the end of the pretreatment and at each desorption stage in transmission mode with an accumulation time of 100 s. The spectra are set to iso-mass (therefore assumed to be iso-thickness) (20 mg exactly). The number of Lewis sites is proportional to the surface area of the peak whose maximum lies around 1450 cm$^{-1}$, including any shoulder. The number of Bronsted sites is proportional to the surface area of the peak whose maximum is located toward 1545 cm$^{-1}$. The ratio of the number of Bronsted sites/number of Lewis sites (B/L) is estimated to be equal to the ratio of the surface areas of two peaks described above. The surface area of peaks at 25° C. is generally used. This B/L ratio is generally calculated starting from the spectrum that is recorded at 25° C. at the end of the pretreatment.

Description of the Process

More specifically, the invention relates to a process for the production of at least one compound that is selected from among the 2, 3-, 4-, 5-, and 6-phenylalkanes by alkylation of an aromatic compound (preferably benzene) by means of at least one olefin that comprises at least 9 carbon atoms per molecule, in the presence of a catalyst that comprises at least one non-zeolitic substrate based on silicated alumina that contains an amount that is more than 6% by weight and less than or equal to 50% by weight of silica ($SiO_2$) and that exhibits the following characteristics:

A mean pore diameter, measured by mercury porosimetry, encompassed between 20 and 140 Å, a total pore volume, measured by mercury porosimetry, encompassed between 0.1 ml/g and 0.6 ml/g, a total pore volume, measured by nitrogen porosimetry, encompassed between 0.1 ml/g and 0.6 ml/g, a BET specific surface area encompassed between 100 and 500 m²/g, a packing density of more than 0.85, a pore volume, measured by mercury porosimetry, encompassed in the pores with a diameter of more than 140 Å, of less than 0.1 ml/g, a pore volume, measured by mercury porosimetry, encompassed in the pores with a diameter of more than 160 Å, of less than 0.1 ml/g, a pore volume, measured by mercury porosimetry, encompassed in the pores with a diameter of more than 200 Å, of less than 0.1 ml/g, a pore volume, measured by mercury porosimetry, encompassed in the pores with a diameter of more than 500 Å, of less than 0.1 ml/g, preferably less than 0.05 m/g, and very preferably less than 0.01 ml/g, an X diffraction diagram that contains at least the main lines that are characteristic of at least one of the transition aluminas contained in the group that consists of the alpha, rho, chi, eta, gamma, kappa, theta and delta aluminas, preferably a pore distribution such that the ratio between volume V2, measured by mercury porosimetry, encompassed between $D_{mean}-30$ Å and $D_{mean}+30$ Å, to the total mercury volume is greater than 0.6, such that volume V3, measured by mercury porosimetry, encompassed in the pores with a diameter of more than $D_{mean}+30$ Å is less than 0.1 ml/g, and such that volume V6, measured by mercury porosimetry, encompassed in the pores with a diameter of more than $D_{mean}+15$ Å is less than 0.2 ml/g, whereby said process is conducted at a temperature of between 30 and 400° C., a pressure of between 0.1 and 10 MPa, an hourly volumetric flow rate of 0.05 to 200 h−1, and an aromatic compound/olefin molar ratio of between 1:1 and 50:1.

Characteristics of the Catalyst

The catalyst that is used in the process according to this invention comprises:

A non-zeolitic substrate with a content by mass of silica ($SiO_2$) that is more than 6% by weight and less than or equal to 50% by weight, preferably encompassed between 10 and 50% by weight, more preferably a silica content of more than 20% by weight and less than 50% by weight and even more preferably more than 20% by weight and less than 40% by weight.

A cationic impurity content that is generally less than 0.1% by weight, preferably less than 0.05% by weight, and even more preferably less than 0.025% by weight. Cationic impurity content is defined as the total alkaline content.

An anionic impurity content that is generally less than 1% by weight, preferably less than 0.5% by weight and even more preferably less than 0.1% by weight.

The silicated alumina that is used in the process according to the invention is preferably a silicated alumina that is homogeneous on the micrometer scale and in which the content of cationic impurities (for example, $Na^+$) is generally less than 0.1% by weight, preferably less than 0.05% by weight and even more preferably less than 0.025% by weight, and the content of anionic impurities (for example $SO_4^{2-}$, $Cl^-$) is generally less than 1% by weight, preferably less than 0.5% by weight, and even more preferably less than 0.1% by weight.

Thus, any process of synthesis of silicated alumina that is known to one skilled in the art that leads to a silicated alumina that is homogeneous on the micrometer scale and in which the cationic impurities (for example $Na^+$) can be brought to less than 0.1%, preferably to a content of less than 0.05% by weight, and even more preferably less than 0.025% by weight, and in which the anionic impurities (for example, $SO_4^{2-}$, $Cl^-$) can be brought to less than 1% and more preferably less than 0.05% by weight is suitable for preparing substrates that can be used in the process according to the invention.

Optionally at least one hydro-dehydrogenating element that is selected from the group that is formed by the noble elements of group VIII or the elements of group VIB of the periodic table, the content by mass of noble metals of group VIII or metals of group VIB, in metallic form or in oxide form, being generally encompassed between 0.005 and 5% by weight, preferably between 0.01 and 3% by weight and even more preferably between 0.05 and 1% by weight.

Optionally at least one halogenated element, preferably selected from the group that is formed by chlorine and fluorine. More preferably, the halogen that is introduced on the catalyst is fluorine. The contents by mass of halogen are encompassed between 0.5 and 10%, preferably between 1 and 5%.

A mean pore diameter, measured by mercury porosimetry, encompassed between 20 and 140 Å, preferably between 40 and 120 Å, and even more preferably between 50 and 100 Å, Preferably a ratio between volume V2, measured by mercury porosimetry, encompassed between $D_{mean}-30$ Å and $D_{mean}+30$ Å, to the total pore volume that is also measured by mercury porosimetry of more than 0.6, more preferably more than 0.7, and even more preferably more than 0.8.

Preferably a volume V3 that is encompassed in the pores with diameters of more than $D_{mean}+30$ Å, measured by mercury porosimetry, of less than 0.1 ml/g, more preferably less than 0.06 ml/g, and even more preferably less than 0.04 ml/g.

Preferably a ratio between volume V5 that is generally encompassed between $D_{mean}-15$ Å and $D_{mean}+15$ Å measured by mercury porosimetry, and volume V2 that is encompassed between $D_{mean}-30$ Å and $D_{mean}+30$ Å, measured by mercury porosimetry, of more than 0.6, more preferably more than 0.7, and even more preferably more than 0.8.

Preferably a volume V6 that is encompassed in the pores with diameters of more than $D_{mean}+15$ Å, measured by mercury porosimetry, of less than 0.2 ml/g, more preferably less than 0.1 ml/g and even more preferably less than 0.05 ml/g.

A total pore volume, measured by mercury porosimetry, encompassed between 0.1 ml/g and 0.6 ml/g, preferably between 0.20 and 0.50 ml/g and even more preferably of more than 0.20 ml/g.

A total pore volume, measured by nitrogen porosimetry, encompassed between 0.1 ml/g and 0.6 ml/g, preferably encompassed between 0.20 and 0.50 ml/g.

A BET specific surface area encompassed between 100 and 500 m²/g, preferably between 150 and 500 m²/g.

An adsorption surface area such that the ratio between the adsorption surface area and the BET surface area is more than 0.5, preferably more than 0.65, and more preferably more than 0.8.

A pore volume, measured by mercury porosimetry, encompassed in the pores with a diameter of more than 140 Å, of less than 0.1 ml/g, preferably less than 0.05 ml/g and even more preferably less than 0.03 ml/g.

A pore volume, measured by mercury porosimetry, encompassed in the pores with a diameter of more than 160 Å, of less than 0.1 ml/g, preferably less than 0.05 ml/g, and even more preferably less than 0.025 ml/g.

A pore volume, measured by mercury porosimetry, encompassed in the pores with a diameter of more than 200 Å, of less than 0.1 ml/g, preferably less than 0.05 ml/g, and even more preferably less than 0.025 ml/g.

A pore volume, measured by mercury porosimetry, encompassed in the pores with a diameter of more than 500 Å, of less than 0.1 ml/g, preferably less than 0.05 ml/g, and very preferably less than 0.01 ml/g.

A packing density of catalysts that is more than 0.85 g/cm³, preferably more than 0.95 g/cm³, very preferably more than 1.025 cm³/g, and even more preferably more than 1.1 g/cm³.

An X diffraction diagram, characterized in that it contains at least the main lines that are characteristic of at least one of the transition aluminas contained in the group that consists of the rho, chi, kappa, eta, gamma, theta and delta aluminas, and preferably characterized in that it contains at least the main lines that are characteristic of at least one of the transition aluminas contained in the group that consists of the gamma, eta, theta and delta alumina, and more preferably characterized in that it contains at least the main lines that are characteristic of the gamma-alumina and eta-alumina, and even more preferably characterized in that it contains the peaks at one d encompassed between 1.39 and 1.40 Å and the peaks at one d encompassed between 1.97 Å and 2.00 Å.

The NMR MAS spectra of the solid of $^{27}$Al of the substrates and catalysts show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm extends between 20 and 110 ppm. This cluster can be decomposed into at least two radicals. The predominant radical of this cluster would correspond to $Al_{IV}$ atoms (tetrahedral). For the substrates and catalysts of this invention, the proportion of octahedral $Al_{VI}$ is more than 50%, preferably more than 60%, and even more preferably more than 70%.

In an embodiment of the invention, the catalyst contains a substrate that comprises at least two silico-aluminum zones, whereby said zones have Si/Al ratios that are less than or greater than the overall Si/Al ratio that is determined by X fluorescence. Thus, a substrate that has an Si/Al ratio that is equal to 0.5 comprises, for example, two silico-aluminum zones; one of the zones has an Si/Al ratio that is determined by TEM (transmission electron microscopy) to be less than 0.5, and the other zone has an Si/Al ratio that is determined by TEM to be between 0.5 and 2.5.

In another embodiment of the invention, the catalyst contains a substrate that comprises a single silico-aluminum zone, whereby said zone has an Si/Al ratio that is equal to the overall Si/Al ratio that is determined by X fluorescence and is less than 2.3.

The catalyst that can be used in the process according to the invention preferably exhibits a bed crushing value, determined according to the Shell method (SMS 1471-74) and characterizing its mechanical resistance, of more than 0.5 MPa.

The acidity of the substrate that can be used in the process according to the invention can advantageously be measured, without this restricting the scope of the invention, by IR tracking of the thermodesorption of the pyridine. Generally, the B/L ratio, as described above, of the substrate is encompassed between 0.05 and 1, preferably between 0.05 and 0.7, very preferably between 0.06 and 0.3, and even more preferably between 0.075 and 0.15.

Processes of Preparation

The catalysts that can be used in the process according to the invention can be prepared according to all the methods that are well known to one skilled in the art.

A preferred process for preparation of the catalyst according to this invention comprises the following stages:

According to a preferred preparation method, the precursor is obtained by direct shaping of the silicated alumina by itself or by shaping the silicated alumina with at least one binder, then drying and calcination. The elements of groups VIB and/or VIII, and optionally those that are selected from among phosphorus, boron, and silicon and optionally the elements of groups VB, and VIIB, are then optionally introduced by any method that is known to one skilled in the art, before or after the shaping and before or after the calcination of the precursor or the catalyst.

The hydrogenating element can be introduced at any stage of the preparation, preferably during the mixing, or very preferably after shaping. The shaping is followed by calcination; the hydrogenating element can also be introduced before or after this calcination. The preparation generally ends by a calcination at a temperature of 250 to 600° C. Another of the preferred methods according to this invention consists in shaping the silicated alumina without a binder after the latter is mixed, then passing the thus obtained paste through a die to form extrudates with a diameter of between 0.4 and 4 mm. The hydrogenating function can then be introduced only in part or in its entirety, at the time of mixing. It can also be introduced by one or more ion exchange operations on the calcined substrate that consists of at least one silicated alumina, optionally shaped with a binder, with solutions that contain the precursor salts of the selected metals.

In a preferred way, the substrate is impregnated by an aqueous solution. The impregnation of the substrate is preferably carried out by the so-called "dry" impregnation method that is well known to one skilled in the art. The impregnation can be carried out in a single stage by a solution that contains all of the constituent elements of the final catalyst.

The catalyst that can be used in the process of this invention can therefore contain at least one noble element of group VIII, such as ruthenium, rhodium, palladium, osmium, iridium or platinum. Among the noble metals of group VIII, it is preferred to use a metal that is selected from the group that is formed by platinum, palladium and ruthenium. A preferred combination of noble elements of group VIII for the catalyst that can be used in the process of this invention is the platinum-palladium combination.

The halogenated elements can be introduced into the catalyst at any level of the preparation and according to any technique that is known to one skilled in the art. The halogenated compounds are preferably added with the help of an aqueous solution that is prepared from corresponding mineral acids, for example HF or HCl (dry impregnation, impregnation by excess, or co-mixing). The use of ammonium fluoride/ammonium chloride ($NH_4F$, $NH_4HF_2$ or $NH_4Cl$) can also be considered, the dry impregnation of the substrates by this type of compound furthermore being the most used method in the scientific literature in the field.

The decomposition of the organofluorine compounds and/or organochlorine compounds on the catalyst is a method that may also be suitable in the invention. This makes it possible to avoid the use of hydrofluoric acid solutions, now regulated.

The noble metals of group VIII of the catalyst of this invention can be present in their entirety or partially in metallic form and/or oxide form and/or sulfide form.

The sources of noble elements of group VIII that can be used are well known to one skilled in the art. Halides, for example chlorides, nitrates, acids such as chloroplatinic acid, oxychlorides such as ammoniacal ruthenium oxychloride, or amines, will be used.

Characteristics of the Substrate

The thus obtained catalyst that can be used in the process according to the invention is prepared, by any technique that is known to one skilled in the art, starting from a substrate whose characteristic are as follows:

The content by mass of silica ($SiO_2$) is more than 6% by weight and less than or equal to 50% by weight, preferably encompassed between 10 and 50% by weight, more preferably a silica content of more than 20% by weight and less than 50% by weight and even more preferably more than 20% by weight and less than 40% by weight.

The cationic impurity content is generally less than 0.1% by weight, preferably less than 0.05% by weight, and even more preferably less than 0.025% by weight. Cationic impurity content is defined as the total alkaline content.

The anionic impurity content that is generally less than 1% by weight, preferably less than 0.5% by weight and even more preferably less than 0.1% by weight.

The mean pore diameter, measured by mercury porosimetry, is encompassed between 20 and 140 Å, preferably between 40 and 120 Å, and even more preferably between 50 and 100 Å.

The ratio between volume V2, measured by mercury porosimetry, encompassed between $D_{mean}-30$ Å and $D_{mean}+30$ Å, to the total pore volume that is also measured by mercury porosimetry, is generally more than 0.6, preferably more than 0.7, and even more preferably more than 0.8.

Volume V3 that is encompassed in the pores with a diameter of more than $D_{mean}+30$ Å, measured by mercury porosimetry, is generally less than 0.1 ml/g, preferably less than 0.06 ml/g, and even more preferably less than 0.04 ml/g.

The ratio between volume V5, measured by mercury porosimetry, encompassed between $D_{mean}-15$ Å and $D_{mean}+15$ Å to volume V2, measured by mercury porosimetry, encompassed between $D_{mean}-30$ Å and $D_{mean}+30$ Å, is generally more than 0.6, preferably more than 0.7, and even more preferably more than 0.8.

Volume 6, encompassed in the pores with diameters of more than $D_{mean}+15$ Å and measured by mercury porosimetry, is generally less than 0.2 ml/g, preferably less than 0.1 ml/g, and even more preferably less than 0.05 ml/g.

The total pore volume, measured by mercury porosimetry, is encompassed between 0.1 ml/g and 0.6 ml/g, preferably encompassed between 0.20 and 0.50 ml/g, and even more preferably more than 0.20 ml/g.

The total pore volume, measured by nitrogen adsorption, is encompassed between 0.1 ml/g and 0.6 ml/g, preferably encompassed between 0.20 and 0.50 ml/g.

The BET specific surface area is encompassed between 100 and 500 m$^2$/g, preferably encompassed between 150 and 500 m$^2$/g.

The adsorption surface area is such that the ratio between the adsorption surface area and the BET surface area is more than 0.5, more preferably more than 0.65, and even more preferably more than 0.8.

The pore volume, measured by mercury porosimetry, encompassed in the pores with a diameter of more than 140 Å, is less than 0.1 ml/g, preferably less than 0.05 ml/g, and even more preferably less than 0.03 ml/g.

The pore volume, measured by mercury porosimetry, encompassed in the pores with a diameter of more than 160 Å, is less than 0.1 ml/g, preferably less than 0.05 ml/g, and even more preferably less than 0.025 ml/g.

The pore volume, measured by mercury porosimetry, encompassed in the pores with a diameter of more than 200 Å, is less than 0.1 ml/g, preferably less than 0.05 ml/g, and even more preferably less than 0.025 ml/g.

The pore volume, measured by mercury porosimetry, encompassed in the pores with a diameter of more than 500 Å, is less than 0.01 ml/g, preferably less than 0.05 ml/g, and very preferably less than 0.01 ml/g.

The X diffraction diagram is characterized in that it contains at least the main lines that are characteristic of at least one of the transition aluminas contained in the group that consists of the alpha, rho, chi, kappa, eta, gamma, theta and delta aluminas, preferably characterized in that it contains at least the main lines that are characteristic of at least one of the transition aluminas contained in the group that consists of gamma, eta, theta and delta alumina, more preferably characterized in that it contains at least the main lines that are characteristic of the gamma-alumina and eta-alumina, and even more preferably characterized in that it contains peaks at one d encompassed between 1.39 and 1.40 Å and peaks at one d encompassed between 1.97 Å and 2.00 Å.

The NMR MAS spectra of the solid of $^{27}Al$ of the substrates show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm extends between 20 and 110 ppm. This cluster can be decomposed into at least two radicals. The predominant radical of this cluster would correspond to $Al_{IV}$ atoms (tetrahedral). For the substrates and catalysts of this invention, the proportion of octahedral $Al_{VI}$ is more than 50%, preferably more than 60%, and even more preferably more than 70%.

In an embodiment of the invention, the substrate comprises at least two silico-aluminum zones having Si/Al ratios that are less than or greater than the overall Si/Al ratio that is determined by X fluorescence. A substrate according to this invention that has an overall Si/Al ratio that is equal to 0.5 comprises, for example, two silico-aluminum zones, one of the zones has an Si/Al ratio that is determined by TEM to be less than 0.5, and the other zone has an Si/Al ratio that is determined by TEM to be between 0.5 and 2.5.

In another embodiment of the invention, the substrate comprises a single silico-aluminum zone that has an Si/Al ratio that is equal to the overall Si/Al ratio that is determined by X fluorescence and is less than 2.3.

The packing density of substrates, after calcination, is more than 0.65 g/cm$^3$, preferably more than 0.72 g/cm$^3$, very preferably more than 0.75 g/cm$^3$, and even more preferably more than 0.78 g/cm$^3$.

The acidity of the substrate according to the invention can advantageously be measured, without restricting the scope of the invention, by IR tracking of the thermodesorption of the pyridine. Generally, the B/L ratio, as described above, of the substrate according to the invention is between 0.05 and 1, preferably between 0.05 and 0.7, very preferably between 0.06 and 0.3, and even more preferably between 0.075 and 0.15.

Preparation of the Substrate

The applicant discovered that the silico-aluminum substrates obtained starting from a mixture at any arbitrary stage of an alumina compound that is partially soluble in acid medium with a totally soluble silica compound or with a totally soluble combination of hydrated alumina and silica, shaping followed by a hydrothermal or heat treatment so as to homogenize on the micrometer scale, and even on the nanometer scale, made it possible to obtain a particularly active catalyst in the process according to the invention. Partially soluble in acid medium is defined as bringing the alumina compound into contact before any addition of totally soluble silica compound or combination with an acid solution, for example, nitric acid or sulfuric acid, causes partial dissolution thereof.

Silica Sources

The silica compounds that are used according to the invention may have been selected from the group that is formed by silicic acid, silicic acid sols, water-soluble alkaline silicates, cationic silicon salts, for example the hydrated sodium metasilicate, Ludox® in ammonia form or in alkaline form, and quaternary ammonium silicates. The silica sol can be prepared according to one of the methods known to one skilled in the art. A decationized orthosilicic acid solution is preferably prepared starting from a water-soluble alkaline silicate by ion exchange on a resin.

Totally Soluble Silica-Alumina Sources

The totally soluble hydrated silicated aluminas that are used according to the invention can be prepared by true coprecipitation under controlled stationary operating conditions (pH, concentration, temperature, average dwell time) by reaction of a basic solution that contains silicon, for example in the form of sodium silicate, optionally of aluminum, for example, in sodium aluminate form with an acid solution that contains at least one aluminum salt, for example aluminum sulfate. At least one carbonate or else $CO_2$ optionally can be added to the reaction medium.

The applicant defines true coprecipitation as a process by which at least one aluminum compound that is totally soluble in basic medium or acid medium as described below, and at least one silicon compound as described below are brought into contact, simultaneously or sequentially, in the presence of at least one precipitating and/or coprecipitating compound so as to obtain a mixed phase that essentially consists of hydrated silica-alumina that is optionally homogenized by intense stirring, shearing, colloidal grinding or else by a combination of these unitary operations. For example, these hydrated silica aluminas may have been prepared according to the teachings of U.S. Pat. No. 2,908,635; U.S. Pat. No. 3,423,332, U.S. Pat. No. 3,433,747, U.S. Pat. No. 3,451,947, U.S. Pat. No. 3,629,152, and U.S. Pat. No. 3,650,988.

The total dissolution of the silica compound or the combination was evaluated approximately according to the following method. A fixed amount (15 g) of the silica compound or the hydrated combination is introduced into a medium of preset pH. The concentration of solid added per liter of suspension is preferably 0.2 mol per liter. The pH of the dispersion solution is at least 12, and it can be obtained by use of an alkaline source. It is preferably advantageous to use NaOH. The mixture is then stirred mechanically by a deflocculant-type turbine stirring mechanism for 30 minutes at 800 rpm. Once the stirring is ended, the mixture is centrifuged for 10 minutes at 3000 rpm. The cake is separated from the supernatant liquid. The solution was filtered on a filter with a porosity of 4 and a diameter of 19 cm. The drying and then the calcination are then initiated at 1000° C. of the two fractions. Then, an equal ratio R is defined by dividing the decanted mass by the mass of the solid in suspension. Totally soluble is defined as a ratio R that is at least more than 0.9.

Alumina Sources

The alumina compounds that are used according to the invention are partially soluble in acid medium. They are selected completely or partially from the group of alumina compounds of general formula $Al_2O_3$, $nH_2O$. It is possible in particular to use hydrated alumina compounds such as: hydrargillite, gibbsite, bayerite, boehmite, pseudo-boehmite, and amorphous or essentially amorphous alumina gels. It is also possible to use the dehydrated forms of these compounds that consist of transition aluminas and that comprise at least one of the phases that is included in the group: rho, chi, eta, gamma, kappa, theta, and delta, which differ essentially by the organization of their crystalline structure. The alpha-alumina that is commonly called corundum can be incorporated in a small proportion in the substrate according to the invention.

This partial dissolution property is a desired property of the invention; it applies to hydrated alumina powders, to sprayed hydrated alumina powders, to dispersions or suspensions of hydrated alumina or to any combination thereof, before any addition of a compound that contains some or all of the silicon.

The partial dissolution of the alumina compound was evaluated approximately according to the following method. A specific amount of the alumina compound in powdered or suspension form is introduced into a preset pH medium. The mixture is then stirred mechanically. Once the stirring is ended, the mixture is left without stirring for 24 hours. Preferably, the $Al_2O_3$ solid concentration that is added per liter of suspension is 0.5 mol per liter. The pH of the dispersion solution is 2 and is obtained by use of $HNO_3$, HCl, or $HClO_4$. Preferably, it is advantageous to use $HNO_3$. The distribution of sedimented and dissolved fractions was followed by metering of aluminum by UV absorption. The supernatants were ultrafiltered (polyether sulfone membrane, Millipore NMWL: 30,000) and digested in concentrated acid. The amount of aluminum in the supernatant corresponds to the non-sedimented alumina compound and the dissolved aluminum and the fraction that is ultrafiltered with dissolved aluminum only. The amount of sedimented particles is derived from the theoretical concentration of aluminum in the dispersion (by considering that all of the solid that is introduced is dispersed) and amounts of boehmite actually dispersed and aluminum in solution.

The alumina precursors that are used according to this invention are therefore distinguished from those that are used in the case of true co-precipitations that are entirely soluble in acid medium: cationic alumina salts, for example aluminum nitrate. The methods that are part of the invention are distinguished from true co-precipitations because one of the elements, in this case the aluminum compound, is partially soluble.

To use the alumina, any alumina compound of general formula $Al_2O_3$, $nH_2O$ can be used. Its specific surface area is between 150 and 600 $m^2/g$. It is possible in particular to use hydrated alumina compounds, such as: hydrargillite, gibbsite, bayerite, boehmite, pseudo-boehmite and amorphous or essentially amorphous alumina gels. It is also possible to use the dehydrated forms of these compounds that consist of transition aluminas and that comprise at least one of the phases that is included in the group: rho, chi, eta, gamma, kappa, theta, delta and alpha, which differ essentially by the organization of their crystalline structure. During heat treatments, these different forms are liable to evolve among themselves, according to a complex relationship that depends on the treatment operating conditions. It is also possible to use the alpha-alumina that is commonly called corundum in measured proportions.

Aluminum hydrate $Al_2O_3$, $nH_2O$ that is more preferably used is boehmite, pseudo-boehmite and the amorphous or essentially amorphous alumina gels. A mixture of these products under any arbitrary combination can also be used.

Boehmite is generally described as an aluminum monohydrate of formula $Al_2O_3$, $nH_2O$ that in reality includes a broad continuum of materials with variable degrees of hydration and organization with more or less well-defined boundaries: the most hydrated gelatinous boehmite, with n able to be more than 2, the pseudo-boehmite or the microcrystalline boehmite with n encompassed between 1 and 2, then crystalline boehmite, and finally boehmite that is well crystallized with large crystals with n close to 1. The morphology of aluminum monohydrate can vary within broad limits between these two acicular or prismatic end forms. An entire set of variable forms can be used between these two forms: chain, boats, interlaced platelets.

The preparation and/or the shaping of the aluminum hydrate thus can constitute the first stage of the preparation of these catalysts. Many patents relate to the preparation and/or the shaping of transition-alumina-based substrates that are obtained from aluminum monohydrate: U.S. Pat. No. 3,520,654; U.S. Pat. No. 3,630,670; U.S. Pat. No. 3,864,461; U.S. Pat. No. 4,154,812; U.S. Pat. No. 4,313,923; DE 3243193; and U.S. Pat. No. 4,371,513.

Relatively pure aluminum hydrates can be used in the form of amorphous powder or crystallized powder or crystallized powder that contains an amorphous portion. The aluminum hydrate can also be introduced in the form of aqueous suspensions or dispersions. The aqueous suspensions or dispersions of aluminum hydrate that are used according to the invention may have the ability to gel or solidify. The aqueous dispersions or suspensions can also be obtained, as is well known to one skilled in the art, by peptization in water or water that is acidified with aluminum hydrates.

The dispersion of aluminum hydrate can be carried out by any process that is known to one skilled in the art: in a batch reactor, a continuous mixer, a mixing machine, or a colloidal mill. Such mixing can be also be carried out in a piston flow reactor and, in particular, in a static mixer. The Lightnin reactors can be cited.

In addition, it is also possible to use as an alumina source an alumina that has been subjected in advance to a treatment that can improve its degree of dispersion. By way of example, it will be possible to improve the dispersion of the alumina source by a preliminary homogenization treatment. For homogenization, it is possible to use at least one of the homogenization treatments described in the following text.

The aqueous dispersions or suspensions of alumina that can be used are, in particular, the aqueous suspensions or dispersions of fine or ultra-fine boehmites that consist of particles that have dimensions in the colloidal range.

Fine or ultra-fine boehmites that are used according to this invention may have been obtained in particular according to French Patents FR 1 261 182 and 1 381 282 or in European Patent Application No. 15 196.

It is also possible to use the aqueous suspensions or dispersions that are obtained from pseudo-boehmite, amorphous alumina gels, aluminum hydroxide gels or ultra-fine hydrargillite gels.

Aluminum monohydrate can be purchased from among a variety of commercial sources of alumina, such as, in particular, PURAL®, CATAPAL®, DISPERAL®, and DISPAL® that are marketed by the SASOL Company or else HIQ® that is marketed by ALCOA, or according to the methods that are known to one skilled in the art: it can be prepared by partial dehydration of aluminum trihydrate by conventional methods or it can be prepared by precipitation. When these aluminas are presented in the form of a gel, they are peptized by water or an acidified solution. In the precipitation, the acid source can be selected, for example, from among at least one of the following compounds: aluminum chloride, aluminum sulfate, or aluminum nitrate. The basic aluminum source can be selected from among the basic aluminum salts such as sodium aluminate and potassium aluminate.

As precipitating agents, sodium hydroxide, sodium carbonate, potassium and ammonia can be used. The precipitating agents are selected such that the alumina source according to this invention and these agents are precipitated together.

According to the acidic or basic nature of the aluminum-based starting compound, the aluminum hydrate is precipitated with the help of a base or an acid that is selected from among, for example, hydrochloric acid, sulfuric acid, sodium or a basic or acidic compound of the aluminum such as those cited above. The two reagents can be aluminum sulfate and sodium aluminate. For an example of a preparation of aluminum alpha-monohydrate that uses aluminum sulfate and sodium aluminate, it is possible to refer in particular to U.S. Pat. No. 4,154,812.

In particular, pseudo-boehmite may have been prepared according to the process that is described in U.S. Pat. No. 3,630,670 by reaction of an alkaline aluminate solution with a mineral acid solution. The pseudo-boehmite may have been prepared in particular according to the process that is described in U.S. Pat. No. 3,630,670 by reaction of an alkaline aluminate solution with a solution of a mineral acid. It may also have been prepared as described in French Patent FR 1 357 830.

In particular, the amorphous alumina gels may have been prepared according to the processes that are described in the article "Alcoa Paper No. 19 (1972) pages 9 to 12" and in particular by reaction of acid aluminate or an aluminum salt or by hydrolysis of aluminum alcoholates or by hydrolysis of basic aluminum salts.

The aluminum hydroxide gels can be in particular those that have been prepared according to the processes that are described in U.S. Pat. No. 3,268,295 and U.S. Pat. No. 3,245,919.

In particular, the aluminum hydroxide gels may be those prepared according to the processes that are described in Patent WO 00/01617 by mixing an aluminum acid source and a base or an aluminum basic source and an acid so as to precipitate an alumina monohydrate, whereby the following stages are:
2. development
3. filtration
4. washing, and
5. drying, processes characterized in that the mixing of stage one is carried out without retromixing.

The ultrafine hydrargillite may have been prepared in particular according to the process that is described in U.S. Pat. No. 1,371,808 by evolving toward a temperature encompassed between ambient temperature and 60° C. for alumina gels in cake form and that contain 0.1 monovalent acid ions relative to the alumina that is counted in $Al_2O_3$ molecules.

It is also possible to use ultra-pure aqueous suspensions or dispersions of boehmite or pseudo-boehmite that are prepared according to a process in which the reaction of an alkaline aluminate is carried out with the carbonic anhydride to form an amorphous aluminum hydroxycarbonate precipitate, the precipitate that is obtained by filtration is separated, and then the latter is washed (the process is described in particular in U.S. Pat. No. 3,268,295).

Then,
a) in a first stage, the precipitate that is washed with amorphous aluminum hydroxycarbonate is mixed with an acid solution, a base or a salt or mixtures thereof; this mixing is carried out by pouring the solution over the hydroxycarbonate, whereby the pH of the thus constituted medium is less than 11,
b) in a second stage, the thus constituted reaction medium is heated to a temperature of less than 90° C. for a period of at least 5 minutes,
c) in a third stage, the medium that results from the second stage is heated to a temperature of between 90° C. et 250° C.

The boehmite and pseudo-boehmite dispersions or suspensions that are obtained according to this process exhibit an alkaline content of less than 0.005% that is expressed in the form of a ratio by weight of alkaline metal oxide/$Al_2O_3$.

When it is desired to produce very pure catalyst substrates, ultra-pure boehmite or pseudo-boehmite suspensions or dispersions that have been obtained according to the process that was described above, or the aluminum hydroxide gels that were prepared starting from the hydrolysis of aluminum alcoholates according to a process of the type that is described in U.S. Pat. No. 2,892,858 are preferably used.

In summary, the production process that leads to such boehmite-type aluminum hydroxide gels obtained as a by-product in the production of alcohol by hydrolysis of an alcoholate or alkoxide of aluminum (Ziegler synthesis) is described. The Ziegler alcohol synthesis reactions are described in particular in U.S. Pat. No. 2,892,858. According to this process, first triethyl aluminum is prepared starting from aluminum, hydrogen and ethylene, whereby the reaction is carried out in two stages with partial recycling of triethyl aluminum.

Ethylene is added into the polymerization stage, and the product that is obtained is then oxidized into aluminum alcoholate, whereby the alcohols are obtained by hydrolysis.

The aluminum hydroxide gels can also be those that were prepared according to the processes described in U.S. Pat. No. 4,676,928-A and U.S. Pat. No. 6,030,599.

The hydrated alumina that is obtained as a by-product of the Ziegler reaction is described in particular in a report of the CONOCO Company dated Jan. 19, 1971.

The dimension of the alumina particles that constitute the alumina source can vary within wide limits. It is generally between 1 and 100 microns.

Methods

The substrate can advantageously be prepared by one of the methods described below.

By way of example, a method of preparation of a silicated alumina that is part of the invention consists in preparing, starting from a water-soluble alkaline silicate, an orthosilicic acid solution ($H_2SiO_4$, $H_2O$) that is decationized by ion exchange, then in simultaneously adding it to a cationic aluminum salt in solution, for example, nitrate, and to ammonia under controlled operating conditions; or else adding the orthosilicic acid solution to the cationic aluminum salt in solution and coprecipitating the solution that is obtained by ammonia under controlled operating conditions leading to a homogeneous product. This silicated alumina hydrogel is mixed with an aluminum hydrate powder or suspension. After filtering and washing, drying with shaping then calcination, preferably in air, in a rotary kiln, at a high temperature and for an adequate period to promote interactions between the alumina and the silica, generally at least two hours, a substrate that fulfills the characteristics of the invention is obtained.

Another method for preparation of silicated alumina according to the invention consists in precipitating the alumina hydrate as above, in filtering it and washing it, then in mixing it with aqueous orthosilicic acid so as to obtain a suspension, which is thoroughly homogenized by vigorous stirring and shearing. An Ultraturrax turbine or else a Staro turbine can be used, or else a colloidal mill, for example a Staro colloidal mill. The homogeneous suspension is then dried by spraying as above, then calcined between 500 and 1200° C. for at least three hours: a silicated alumina substrate that can be used in the process according to the invention is obtained.

Another method that is part of the invention consists in preparing as above a decationized solution of orthosilicic acid then in adding it simultaneously or consecutively to an alumina compound, for example an aluminum hydrate in powdered form or in an acidified suspension form. To increase the diameter of the pores of the final silicated alumina substrate, at least one basic compound can optionally be added to the reaction medium. After an intense homogenization of the suspension by stirring, optional adjustment by filtration of the content of dry material then optionally rehomogenization, the product is dried with simultaneous or consecutive shaping, then calcined as above.

Another method that is also part of the invention consists in preparing an aqueous alumina suspension or dispersion, for example an aluminum monohydrate, then in adding it simultaneously or consecutively to a silica compound, for example a sodium silicate. To increase the final diameter of the pores of the silicated alumina-based substrate, at least one basic compound can optionally be added to the reaction medium. The substrate is obtained by filtration and washing, optionally washing by an ammonia solution to extract the residual sodium by ion exchange, drying with simultaneous or consecutive shaping. After drying with shaping, then calcination as above, a substrate that fulfills the characteristics of the invention is obtained. The size of the alumina particles used is preferably between 1 and 100 microns to obtain good homogenization of the silicated alumina-based substrate according to the invention.

To increase the diameter of the mesopores of the silicated alumina-based substrate, it may be particularly advantageous, as U.S. Pat. No. 4,066,574 teaches us, to prepare an aqueous alumina suspension or dispersion, for example, an aluminum monohydrate, and then to neutralize by a basic solution, for example ammonia, then to add it simultaneously or consecutively to a silica compound, for example a decationized orthosilicic acid solution. After an intensive homogenization of the suspension by intense stirring, optional adjustment by filtration of the dry material content then rehomogenization, the product is dried with simultaneous or consecutive shaping, then calcined as above. This method is also part of the methods that are used according to the invention.

In the specification of the above-mentioned methods, homogenization is used to describe putting back into solution a product that contains a solid fraction, for example a suspension, a powder, a filtered precipitate, then its dispersion under intense stirring. The homogenization of a dispersion is a process that is well known to one skilled in the art. Said homogenization can be carried out by any process that is known to one skilled in the art: by way of example, in a batch reactor, a continuous mixer, or a mixing machine. Such a mixing can be carried out in a piston flow reactor and in particular in a static reactor. The Lightnin reactors can be cited. An Ultraturrax® turbine or else a Staro® turbine can be used, or else a colloidal mill, for example a Staro colloidal mill. The commercial colloidal mills IKA® can also be used.

In all of the above-mentioned methods, it may optionally be desirable to add, during any arbitrary stage of the preparation, a minor proportion of at least one stabilizing element that is selected from the group that is formed by zirconia and titanium. The stabilizing element is preferably added in the form of a soluble salt.

Shaping of the Substrates and Catalysts

The substrate can be obtained by shaping the silicated alumina by any technique that is known to one skilled in the art. The shaping can be carried out, for example, by extrusion, by pelletizing, by the drop (oil-drop) coagulation method, by turntable granulation or by any other method that is well known to one skilled in the art.

The shaping can also be carried out in the presence of various components of the catalyst and extrusion of the mineral paste that is obtained, by pelletizing, shaping in the form of balls with a rotating groove or with a drum, drop coagulation, oil-drop, oil-up or any other known process for agglomeration of a powder that contains alumina and optionally other ingredients that are selected from among those that are mentioned above.

The catalysts that are used according to the invention have the shape of spheres or extrudates. It is advantageous, however, that the catalyst comes in the form of extrudates with a diameter of between 0.5 and 5 mm and more particularly between 0.7 and 2.5 mm. The shapes are cylindrical (which may or may not be hollow), twisted cylindrical, multilobar (2, 3, 4 or 5 lobes, for example), and rings. The cylindrical shape is preferably used, but any other shape may be used.

Furthermore, these substrates that are used according to this invention may have been treated, as is well known to one skilled in the art, by additives to facilitate the shaping and/or to improve the final mechanical properties of the silico-aluminum substrates. By way of example of additives, it is possible to cite in particular cellulose, carboxymethylcellulose, carboxy-ethyl-cellulose, tall oil, xanthan gums, surfactants, flocculant agents such as polyacrylamides, carbon black, starches, stearic acid, polyacrylic alcohol, polyvinyl alcohol, biopolymers, glucose, polyethylene glycols, etc.

The adjustment of the porosity that is characteristic of the substrates of the invention is carried out partially during this shaping stage of the substrate particles.

The shaping can be carried out by using techniques for shaping the catalysts, known to one skilled in the art, such as, for example: extrusion, sugar-coating, spray-drying or else pelletizing.

It is possible to add or to withdraw water to adjust the viscosity of the paste that is to be extruded. This stage can be carried out at any stage of the mixing stage.

To adjust the content of solid material of the paste that is to be extruded so as to make it extrudable, it is also possible to add a compound that is solid for the most part and preferably an oxide or a hydrate. A hydrate will preferably be used, and even more preferably, an aluminum hydrate will be used. The fire loss of this hydrate will be more than 15%.

The acid content added in the mixing before the shaping is less than 30%, preferably between 0.5 and 20% by weight of the anhydrous silica and alumina mass that is engaged in the synthesis.

The extrusion can be carried out by any conventional tool, available commercially. The paste that is obtained from mixing is extruded through a dye, for example with the help of a piston or a single- or double-extrusion screw. This extrusion stage can be carried out by any method that is known to one skilled in the art.

The substrate extrudates of the invention generally have a resistance to the crushing of at least 70 N/cm and preferably greater than or equal to 100 N/cm.

Calcination of the Substrate

The drying is carried out by any technique that is known to one skilled in the art.

To obtain the substrate of this invention, it is preferable to calcinate preferably in the presence of molecular oxygen, for example by carrying out a flushing with air, at a temperature that is less than or equal to 1100° C. At least one calcination can be carried out after any arbitrary stage of the preparation. This treatment can be performed, for example, in a flushed bed, in a swept bed or in static atmosphere. For example, the furnace that is used can be a rotary kiln or a vertical furnace with radial flushed layers. The calcination conditions: the temperature and duration depend mainly on the maximum temperature of use of the catalyst. The preferred conditions of calcination are between more than one hour at 200° C. to less than one hour at 1100° C. The calcination can be performed in the presence of water vapor. The final calcination optionally can be carried out in the presence of an acidic or basic vapor. For example, the calcination can be carried out under partial pressure of ammonia.

Post-Synthesis Treatments

Post-synthesis treatments can be carried out so as to improve the properties of the substrate, in particular its homogeneity as defined above.

According to the invention, the substrate thus can optionally be subjected to a hydrothermal treatment in a confined atmosphere. Hydrothermal treatment in a confined atmosphere is defined as a treatment by passage with an autoclave in the presence of water under a temperature that is higher than the ambient temperature.

During this hydrothermal treatment, it is possible to treat the shaped silicated alumina in different ways. Thus, it is possible to impregnate the silicated alumina with acid, prior to its passage to the autoclave, whereby autoclaving of the silicated alumina is done either in vapor phase or in liquid phase, whereby this vapor phase or liquid phase of the autoclave may or may not be acid. This impregnation, prior to the autoclaving, may or may not be acid. This impregnation, prior to the autoclaving, can be carried out in the dry state or by immersion of the silicated alumina in an acidic aqueous solution. Dry impregnation is defined as bringing the alumina into contact with a solution volume that is less than or equal to the total pore volume of the treated alumina. The impregnation is preferably carried out in the dry state.

The autoclave is preferably a rotary-basket autoclave such as the one that is defined in Patent Application EP-A-0 387 109.

The temperature during the autoclaving can be between 100 and 250° C. for a period of time of between 30 minutes and 3 hours.

Process for the Production of Phenylalkanes and Embodiments

The invention relates to a process for the production of at least one compound that is selected from among the 2-, 3-, 4-, 5-, and 6-phenylalkanes by alkylation of an aromatic compound (preferably benzene) by means of at least one olefin that comprises at least 9 carbon atoms per molecule, in the presence of a catalyst that comprises at least one non-zeolitic substrate with a silicated alumina base that contains an amount of more than 6% by weight and less than or equal to 50% by weight of silica ($SiO_2$) and that exhibits the following characteristics:

A mean pore diameter, measured by mercury porosimetry, encompassed between 20 and 140 Å, a total pore volume, measured by mercury porosimetry, encompassed between 0.1 ml/g and 0.6 ml/g, a total pore volume, measured by nitrogen porosimetry, encompassed between 0.1 ml/g and 0.6 ml/g, a BET specific surface area encompassed between 100 and 500 $m^2/g$, a packing density of more than 0.85, a pore volume, measured by mercury porosimetry, encompassed in the pores with a diameter of more than 140 Å, of less than 0.1 ml/g, a pore volume, measured by mercury porosimetry, encompassed in the pores with a diameter of more than 160 Å, of less than 0.1 ml/g, a pore volume, measured by mercury porosimetry, encompassed in the pores with a diameter of more than 200 Å, of less than 0.1 ml/g, a pore volume, measured by mercury porosimetry, encompassed in the pores with a diameter of more than 500 Å, of less than 0.1 ml/g, preferably less than 0.05 ml/g, and very preferably less than 0.01 ml/g, an X diffraction diagram that contains at least the main lines that are characteristic of at least one of the transition aluminas contained in the group that consists of the alpha, rho, chi, eta, gamma, kappa, theta and delta aluminas, preferably a pore distribution, such that the ratio between volume V2, measured by mercury porosimetry, encompassed between $D_{mean}-30$ Å and $D_{mean}+30$ Å, to the total mercury volume is more than 0.6, such that volume V3, measured by mercury porosimetry, encompassed in the pores with a diameter of more than $D_{mean}+30$ Å, is less than 0.1 ml/g, and such that volume V6, measured by mercury porosimetry, encompassed in the pores with a diameter of more than $D_{mean}+15$ Å, is less than 0.2 ml/g, whereby said process is carried out at a temperature of between 30 and 400° C., a pressure of between 0.1 and 10 MPa, an hourly volumetric flow rate of 0.50 to 200 h−1, and an aromatic compound/olefin molar ratio of between 1:1 and 50:1.

In an embodiment of the process of the invention, the reactions of alkylation and transalkylation take place together in the same reaction zone (i.e., in the same reactor in the presence of the same catalyst).

In this variant of the process according to the invention, in a reaction zone, the aromatic compound is preferably reacted with a feedstock that contains at least one olefin, for example linear, upon contact with a catalyst that comprises a silicated alumina that has the characteristics defined previously (alkylation reaction), then the product that is obtained is fractionated so as to collect separately a first fraction that contains unconverted aromatic compound, a second fraction that contains at least one olefin, for example linear, initially present in the feedstock (unconverted), a third fraction that contains the 2-, 3-, 4-, 5- and 6-phenylalkanes, and a fourth fraction that contains at least one poly-alkylaromatic compound (or poly-alkylaromatic fraction), whereby the latter is then most often at least partially recycled to said reaction zone where it reacts with the aromatic compound upon contact with said catalyst, so as to be at least partially transalkylated (transalkylation reaction), and a mixture of 2-, 3-, 4-, 5- and 6-phenylalkanes is collected.

The first fraction that contains the unconverted aromatic compound is preferably at least partially recycled to said reaction zone. Likewise, the second fraction that contains at least one unconverted, preferably linear, olefin is preferably at least partially recycled to said reaction zone.

The recycled part of the fourth fraction that for the most part contains in general at least one dialkylaromatic compound is preferably essentially free of heavy alkylaromatic compounds, which can be eliminated by fractionation.

The aromatic compound that is used in this variant of the process according to the invention is preferably benzene.

The alkylation reaction of the process according to this invention can be conducted in the presence of hydrogen, in particular in the case where the catalyst contains a noble element of group VIII.

The process according to this invention can be carried out, for the alkylation stage, at a temperature of between 30 and 400° C., under a pressure of 0.1 to 10 MPa, with a liquid hydrocarbon flow (hourly volumetric flow rate) of about 0.5 to 200 volumes per volume of catalyst and per hour and with an aromatic compound/olefin molar ratio of between 1:1 and 50:1.

In the implementation of the invention that comprises a second separate transalkylation stage, the second stage can be carried out at a temperature of between about 100 and 500° C., preferably between 150 and 400° C., under a pressure of between about 1.5 and 10 MPa (preferably 2 to 7 MPa), with a liquid hydrocarbon flow (volumetric flow rate) of about 0.5 to 5 volumes per volume of catalyst and per hour, and with an aromatic compound/polyalkylaromatic compound molar ratio of about 2:1 to 50:1.

The following examples illustrate this invention without, however, limiting its scope.

EXAMPLE 1

Preparation and Shaping of a Silica-Alumina According to the Invention (SA1)

The silica-alumina SA1 according to the invention is prepared from a totally soluble silica-alumina that is obtained by any technique that is known to one skilled in the art, to which is added a sodium silicate solution. The method of operation is as follows: in a first step, a 30% sulfuric acid solution is added to a sodium silicate solution. The amount of $H_2SO_4$ is defined so as to work at a set neutralization rate. The addition is done in two minutes while being stirred at 600 rpm. The synthesis temperature is 60° C. The development period was set at 30 minutes. The stirring is maintained at 600 rpm, and the temperature is that of the preceding stage. Then, $Al_2(SO_4)_3$ (500 ml) is added, and the concentration is set by the desired alumina content. The pH is not regulated and is set by the desired alumina content. The addition is done in 10 minutes. The stirring is still set at 600 rpm, and the temperature is the same as that of the preceding stages. Then, ammonia is added. The gel that is obtained is filtered by displacement. The washing is done with water at 60° C., 3 kg of water per kg of solid that is contained in the gel. Then, an exchange with ammonium nitrate $NH_4NO_3$ (138.5 g/l) at 60° C. and 1.5 l per kg of solid that is contained in the gel is carried out. Finally, a supplemental washing with water at 60° C. is done by displacement, 3 kg of water per kg of solid that is contained in the gel. The gel that is obtained from this stage is mixed with Pural boehmite powder such that the final composition of the mixed substrate made of anhydrous product is, at this stage of the synthesis, equal to 50% $Al_2O_3$-50% $SiO_2$. The mixing is done in a Z-arm mixing machine. The extrusion is carried out by passing the paste through a die that is equipped with orifices with a 1.4 mm diameter. The thus obtained extrudates are dried at 150° C., calcined at 550° C., then calcined at 700° C. in the presence of water vapor.

The characteristics of the substrate are as follows:

The composition of the substrate is 50.12% $Al_2O_3$-49.88% $SiO_2$.

The BET surface area is 254 m²/g.

The total pore volume, measured by nitrogen adsorption, is 0.43 ml/g.

The mean pore diameter, measured by mercury porosimetry, is 65 Å.

The ratio between volume V2, measured by mercury porosimetry, encompassed between $D_{mean}$–30 Å and $D_{mean}$+30 Å to the total mercury volume is 0.91.

Volume V3, measured by mercury porosimetry, encompassed in the pores with a diameter of more than $D_{mean}$+30 Å is 0.03 ml/g.

Volume V6, measured by mercury porosimetry, encompassed in the pores with a diameter of more than $D_{mean}$+15 Å is 0.047 ml/g.

The ratio between the adsorption surface area and the BET surface area is 0.76.

The pore volume, measured by mercury porosimetry, encompassed in the pores with a diameter of more than 140 Å is 0.015 ml/g.

The pore volume, measured by mercury porosimetry, encompassed in the pores with a diameter of more than 160 Å is 0.013 ml/g.

The pore volume, measured by mercury porosimetry, encompassed in the pores with a diameter of more than 200 Å is 0.011 ml/g.

The pore volume, measured by mercury porosimetry and encompassed in the pores with a diameter of more than 500 Å, is 0.001 ml/g.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å.

The B/L ratio of the substrate is 0.12.

The packing density of the catalyst is 1.05 g/cm³.

The atomic sodium content is 310+/–20 ppm. The atomic sulfur content is 1600 ppm.

The NMR MAS spectra of the solid of $^{27}Al$ of the catalysts show two clusters of separate peaks. A first type of aluminum whose maximum resonates toward 10 ppm extends between –100 and 20 ppm. The position of the maximum suggests that these radicals are essentially of $Al_{VI}$ type (octahedral). A second type of minority aluminum whose maximum resonates toward 60 ppm extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 67%.

The catalyst contains two silico-aluminum zones, whereby said zones have Si/Al ratios that are less than or greater than the overall Si/Al ratio that is determined by X fluorescence. One of the zones has an Si/Al ratio that is determined by TEM to be 0.7, and the other zone has an Si/Al ratio that is determined by TEM to be 0.98.

EXAMPLE 2

Preparation of a Silica-Alumina According to the Invention (SA2)

The SA2 substrate is prepared starting from the SA1 substrate in the form of extrudates that are dried and calcined by the impregnation of TEOS (tetraethoxysilane) according to the method that is described by B. Beguin, E. Garbowski, and M. Primet in "Journal of Catalysis," page 595, Volume 127, 1991. Then, the impregnated extrudates are dried at 120° C. for 15 hours, calcined at 530° C. under a stream of dry air for 2 hours, then calcined at 700° C. in the presence of water vapor.

The thus obtained sample is dubbed SA2.

The thus obtained extrudates are dried at 150° C., then calcined at 550° C.

The characteristics of the SA2 substrate are as follows:

The composition of the substrate is 52.3% $Al_2O_3$-47.7% $SiO_2$.

The BET surface area is 282 m²/g.

The total pore volume, measured by nitrogen adsorption, is 0.41 ml/g.

The mean pore diameter, measured by mercury porosimetry, is 59 Å.

The ratio between volume V2, measured by mercury porosimetry, encompassed between $D_{mean}$–30 Å and $D_{mean}$+30 Å, to the total mercury volume is 0.90.

Volume V3, measured by mercury porosimetry, encompassed in the pores with a diameter of more than $D_{mean}+30$ Å, is 0.035 ml/g.

Volume V6, measured by mercury porosimetry, encompassed in the pores with a diameter of more than $D_{mean}+15$ Å, is 0.04 ml/g.

The ratio between the adsorption surface area and the BET surface area is 0.75.

The pore volume, measured by mercury porosimetry, encompassed in the pores with a diameter of more than 140 Å is 0.011 ml/g.

The pore volume, measured by mercury porosimetry, encompassed in the pores with a diameter of more than 160 Å is 0.01 ml/g.

The pore volume, measured by mercury porosimetry, encompassed in the pores with a diameter of more than 200 Å is 0.009 ml/g.

The pore volume, measured by mercury porosimetry, encompassed in the pores with a diameter of more than 500 Å is 0.001 ml/g.

The B/L ratio of the substrate is 0.13.

The packing density of the catalyst is 1.07 g/cm$^3$.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å. The atomic sodium content is 300+/−20 ppm. The atomic sulfur content is 1500 ppm.

The NMR MAS spectra of the solid of $^{27}$Al of the catalysts show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm [and that] extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 67%.

The catalyst contains two silico-aluminum zones, whereby said zones have Si/Al ratios that are less than or greater than the overall Si/Al ratio that is determined by X fluorescence. One of the zones has an Si/Al ratio that is determined by TEM to be 0.72, and the other zone has an Si/Al ratio that is determined by TEM to be 0.99.

EXAMPLE 3

Preparation and Shaping of a Silica-Alumina According to the Invention (SA3)

An alumina hydrate is prepared according to the teachings of U.S. Pat. No. 3,124,418. After filtration, the freshly prepared precipitate is mixed with a silicic acid solution that is prepared by decationizing resin exchange. The proportions of the two solutions are adjusted so as to reach a composition of 70% $Al_2O_3$-30% $SiO_2$ on the final substrate. This mixture is quickly homogenized in a commercial colloidal mill in the presence of nitric acid such that the nitric acid content of the suspension at the mill outlet is 8% relative to the silica-alumina mixed solid. Then, the suspension is conventionally dried in a sprayer in a conventional way from 300° C. to 60° C. The thus prepared powder is shaped in a Z-arm in the presence of 8% nitric acid relative to the anhydrous product. The extrusion is carried out by passing the paste through a die that is equipped with orifices with a 1.4 mm diameter. The thus obtained extrudates are dried at 150° C., then calcined at 550° C., then calcined at 750° C. in the presence of water vapor.

The characteristics of the SA3 substrate are as follows:

The composition of the silica-alumina substrate is 69.5% $Al_2O_3$ and 30.5% $SiO_2$.

The BET surface area is 250 m$^2$/g.

The total pore volume, measured by nitrogen adsorption, is 0.45 ml/g.

The mean pore diameter, measured by mercury porosimetry, is 70 Å.

The ratio between volume V2, measured by mercury porosimetry, encompassed between $D_{mean}$−30 Å and $D_{mean}$+30 Å to the total mercury volume is 0.9.

Volume V3, measured by mercury porosimetry, encompassed in the pores with diameters of more than $D_{mean}+30$ Å is 0.021 ml/g.

Volume V6, measured by mercury porosimetry, encompassed in the pores with diameters of more than $D_{mean}+15$ Å, is 0.035 ml/g.

The ratio between the adsorption surface area and the BET surface area is 0.82.

The pore volume, measured by mercury porosimetry, encompassed in the pores with a diameter of more than 140 Å is 0.015 ml/g.

The pore volume, measured by mercury porosimetry, encompassed in the pores with a diameter of more than 160 Å is 0.01 ml/g.

The pore volume, measured by mercury porosimetry, encompassed in the pores with a diameter of more than 200 Å is 0.007 ml/g.

The pore volume, measured by mercury porosimetry, encompassed in the pores with a diameter of more than 500 Å is 0.001 ml/g.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å.

The B/L ratio of the substrate is 0.11.

The packing density of the catalyst is 1.06 g/cm$^3$.

The atomic sodium content is 250+/−20 ppm. The atomic sulfur content is 2000 ppm.

The NMR MAS spectra of the solid of $^{27}$Al of the catalysts show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 69%.

The catalyst contains a single silico-aluminum zone with an Si/Al ratio that is determined by TEM microprobe to be 0.37.

EXAMPLE 4

Preparation of a Silica-Alumina According to the Invention (SA4)

The SA4 substrate is prepared starting from the SA3 substrate, in the form of dried and calcined extrudates, by impregnation of TEOS (tetraethoxysilane) according to the method that is described by B. Beguin, E. Garbowski, and M. Primet in "Journal of Catalysis," page 595, Volume 127, 1991. Then, the impregnated extrudates are dried at 120° C. for 15 hours and calcined at 530° C. under a stream of dry air for 2 hours, then at 700° C. The thus obtained sample is dubbed SA4.

The characteristics of the SA4 substrate are as follows:

The composition of the silica-alumina substrate is 67.5% $Al_2O_3$ and 33.5% $SiO_2$.

The BET surface area is 280 $m^2/g$.

The total pore volume, measured by nitrogen adsorption, is 0.43 ml/g.

The mean pore diameter, measured by mercury porosimetry, is 73 Å.

The ratio between volume V2, measured by mercury porosimetry, encompassed between $D_{mean}-30$ Å and $D_{mean}+30$ Å to the total mercury volume is 0.85.

Volume V3, measured by mercury porosimetry, encompassed in the pores with a diameter of more than $D_{mean}+30$ Å is 0.019 ml/g.

Volume V6, measured by mercury porosimetry, encompassed in the pores with a diameter of more than $D_{mean}+15$ Å, is 0.032 ml/g.

The ratio between the adsorption surface area and the BET surface area is 0.8.

The pore volume, measured by mercury porosimetry, encompassed in the pores with a diameter of more than 140 Å is 0.013 ml/g.

The pore volume, measured by mercury porosimetry, encompassed in the pores with a diameter of more than 160 Å is 0.009 ml/g.

The pore volume, measured by mercury porosimetry, encompassed in the pores with a diameter of more than 200 Å is 0.006 ml/g.

The pore volume, measured by mercury porosimetry, encompassed in the pores with a diameter of more than 500 Å, is 0.001 ml/g.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å.

The atomic sodium content is 240+/−20 ppm. The atomic sulfur content is 1950 ppm.

The B/L ratio of the substrate is 0.12.

The packing density of the catalyst is 1.08 $g/cm^3$.

The NMR MAS spectra of the solid of $^{27}Al$ of the catalysts show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 69%.

The catalyst contains a single silico-aluminum zone, with an Si/Al ratio that is determined by TEM microprobe to be 0.37.

EXAMPLE 5

Preparation and Shaping of a Silica-Alumina According to the Invention (SA5)

The aluminum hydroxide powder was prepared according to the process described in the patent WO 00/01617. The mean particle size of the aluminum hydroxide particles measured by laser granulometry is 40 microns. This powder is mixed with a silica sol that is prepared by decationizing resin exchange, then filtered on a resin with a pore size of 2. The concentrations of silica sol and aluminum hydroxide powder are adjusted so as to obtain a final composition of 60% $Al_2O_3$ and 40% $SiO_2$. The shaping is carried out in the presence of 15% nitric acid relative to the anhydrous product. The mixing is done in a Z-arm mixing machine. The extrusion is carried out by passing the paste through a die that is equipped with orifices with a 1.4 mm diameter. The thus obtained extrudates are dried at 150° C., then calcined at 550° C., then calcined at 750° C. in the presence of water vapor.

The characteristics of the substrate are as follows:

The composition of the silica-alumina substrate is 59.7% $Al_2O_3$ and 40.3% $SiO_2$.

The BET surface area is 248 $m^2/g$.

The total pore volume, measured by nitrogen adsorption, is 0.46 ml/g.

The mean pore diameter, measured by mercury porosimetry, is 69 Å.

The ratio between volume V2, measured by mercury porosimetry, encompassed between $D_{mean}-30$ Å and $D_{mean}+30$ Å to the total mercury volume is 0.9.

Volume V3, measured by mercury porosimetry, encompassed in the pores with a diameter of more than $D_{mean}+30$ Å is 0.022 ml/g.

Volume V6, measured by mercury porosimetry, encompassed in the pores with a diameter of more than $D_{mean}+15$ Å is 0.031 ml/g.

The ratio between the adsorption surface area and the BET surface area is 0.83.

The pore volume, measured by mercury porosimetry, encompassed in the pores with a diameter of more than 140 Å is 0.012 ml/g.

The pore volume, measured by mercury porosimetry, encompassed in the pores with a diameter of more than 160 Å is 0.0105 ml/g.

The pore volume, measured by mercury porosimetry, encompassed in the pores with a diameter of more than 200 Å is 0.0065 ml/g.

The pore volume, measured by mercury porosimetry, encompassed in the pores with a diameter of more than 500 Å is 0.001 ml/g.

The B/L ratio of the substrate is 0.12.

The packing density of the catalyst is 1.08 $g/cm^3$.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å.

The atomic sodium content is 200+/−20 ppm. The atomic sulfur content is 800 ppm.

The NMR MAS spectra of the solid of $^{27}Al$ of the catalysts show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 70%.

The catalyst contains two silico-aluminum zones, whereby said zones have Si/Al ratios that are less than or greater than the overall Si/Al ratio that is determined by X fluorescence. One of the zones has an Si/Al ratio that is determined by TEM to be 0.22, and the other zone has an Si/Al ratio that is determined by TEM to be 0.85.

EXAMPLE 6

Preparation of a Silica-Alumina According to the Invention (SA6)

The SA6 substrate is prepared starting from the SA5 substrate in the form of dried and calcined extrudates. After cooling, the SA5 sample is brought into contact with an ethanolic solution of tetraethyl orthosilicate $Si(OC_2H_5)_4$. This contact is carried out at ambient temperature for 2 hours while being stirred. The solvent is then evaporated under reduced pressure. Then, the impregnated extrudates are dried at 120° C. for 15 hours and calcined at 530° C. under a stream of dry air for 2 hours, then calcined at 700° C. in the presence of water vapor.

The thus obtained sample is dubbed SA6.

The thus obtained extrudates are dried at 150° C., calcined at 550° C.

The characteristics of the substrate are as follows:

The composition of the silica and alumina substrate is 56.38% $Al_2O_3$ and 43.62% $SiO_2$.

The BET surface area is 280 m$^2$/g.

The total pore volume, measured by nitrogen adsorption, is 0.405 ml/g.

The mean pore diameter, measured by mercury porosimetry, is 60 Å.

The ratio between volume V2, measured by mercury porosimetry, encompassed between $D_{mean}$–30 Å and $D_{mean}$+30 Å, to the total mercury volume is 0.9.

Volume V3, measured by mercury porosimetry, encompassed in the pores with a diameter of more than $D_{mean}$+30 Å, is 0.02 ml/g.

Volume V6, measured by mercury porosimetry, encompassed in the pores with a diameter of more than $D_{mean}$+15 Å, is 0.027 ml/g.

The ratio between the adsorption surface area and the BET surface area is 0.8.

The pore volume, measured by mercury porosimetry, encompassed in the pores with a diameter of more than 140 Å is 0.011 ml/g.

The pore volume, measured by mercury porosimetry, encompassed in the pores with a diameter of more than 160 Å is 0.01 ml/g.

The pore volume, measured by mercury porosimetry, encompassed in the pores with a diameter of more than 200 Å is 0.006 ml/g.

The pore volume, measured by mercury porosimetry, encompassed in the pores with a diameter of more than 500 Å is 0.001 ml/g.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å.

The B/L ratio of the substrate is 0.13.

The packing density of the catalyst is 1.09 g/cm$^3$.

The atomic sodium content is 200+/–20 ppm. The atomic sulfur content is 800 ppm.

The NMR MAS spectra of the solid of $^{27}$Al of the catalysts show two clusters of separate peaks. A first type of aluminum whose maximum resonates toward 10 ppm extends between –100 and 20 ppm. The position of the maximum suggests that these radicals are essentially of $Al_{VI}$ type (octahedral). A second type of minority aluminum whose maximum resonates toward 60 ppm extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 70%.

The catalyst contains two silico-aluminum zones, whereby said zones have Si/Al ratios that are less than or greater than the overall Si/Al ratio that is determined by X fluorescence. One of the zones has an Si/Al ratio that is determined by TEM to be 0.23, and the other zone has an Si/Al ratio that is determined by TEM to be 0.86.

EXAMPLE 7

Preparation and Shaping of a Silica-Alumina According to the Invention (SA7)

The SA7 substrate is obtained in the following manner.

The silica-alumina gels are prepared by mixing the sodium silicate and water by sending this mixture over an ion exchange resin. A solution of aluminum chloride hexahydrate in water is added to the decationized silica sol. So as to obtain a gel, ammonia is added, then the precipitate is filtered, and washing with a water and concentrated ammonia solution is carried out until the conductivity of the washing water is constant. The gel that is obtained from this stage is mixed with the Pural boehmite powder so that the final composition of the mixed substrate of anhydrous product is, in this stage of the synthesis, equal to 60% $Al_2O_3$-40% $SiO_2$. This suspension is passed into a colloidal mill in the presence of nitric acid. The added nitric acid content is adjusted so that the percentage at the outlet of the nitric acid mill is 8% relative to the mixed solid oxide mass. This mixture is then filtered so as to reduce the amount of water in the mixed cake. Then, the cake is mixed in the presence of 10% nitric acid and then extruded. The mixing is done in a Z-arm mixing machine. The extrusion is carried out by passing the paste through a die that is equipped with orifices with a 1.4 mm diameter. The extrudates that are thus obtained are dried at 150° C., then calcined at 550° C., then calcined at 700° C. in the presence of water vapor.

The characteristics of the SA7 substrate are as follows:

The composition of the silica-alumina substrate is 60.7% $Al_2O_3$ and 39.3% $SiO_2$.

The BET surface area is 258 m$^2$/g.

The total pore volume, measured by nitrogen adsorption, is 0.47 ml/g.

The mean pore diameter, measured by mercury porosimetry, is 69 Å.

The ratio between volume V2, measured by mercury porosimetry, encompassed between $D_{mean}$–30 Å and $D_{mean}$+30 Å, to the total mercury volume is 0.89.

Volume V3, measured by mercury porosimetry, encompassed in the pores with a diameter of more than $D_{mean}$+30 Å, is 0.032 ml/g.

Volume V6, measured by mercury porosimetry, encompassed in the pores with a diameter of more than $D_{mean}$+15 Å is 0.041 ml/g.

The ratio between the adsorption surface area and the BET surface area is 0.83.

The pore volume, measured by mercury porosimetry, encompassed in the pores with a diameter of more than 140 Å is 0.012 ml/g.

The pore volume, measured by mercury porosimetry, encompassed in the pores with a diameter of more than 160 Å is 0.0082 ml/g.

The pore volume, measured by mercury porosimetry, encompassed in the pores with a diameter of more than 200 Å is 0.0063 ml/g.

The pore volume, measured by mercury porosimetry, encompassed in the pores with a diameter of more than 500 Å is 0.001 ml/g.

The B/L ratio of the substrate is 0.11.

The packing density of the catalyst is 1.06 g/cm$^3$.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å.

The atomic sodium content is 200+/−20 ppm. The atomic sulfur content is 800 ppm.

The NMR MAS spectra of the solid of $^{27}$Al of the catalysts show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 70%.

The catalyst contains a single silico-aluminum zone with an Si/Al ratio that is determined by TEM microprobe to be 0.63.

EXAMPLE 8

Preparation of a Silica-Alumina According to the Invention (SA8)

The SA8 substrate is prepared starting from the SA7 substrate in the form of dried and calcined extrudates. After cooling, the SA7 sample is brought into contact with an ethanolic solution of tetraethyl orthosilicate Si(OC$_2$H$_5$)$_4$. This contact is carried out at ambient temperature for 2 hours while being stirred. The solvent is then evaporated under reduced pressure. Then, the impregnated extrudates are dried at 120° C. for 15 hours and calcined at 530° C. under a stream of dry air for 2 hours. The sample that is thus obtained is dubbed SA8.

The characteristics of the SA8 substrate are as follows:

The composition of the silica-alumina substrate is 57.3% Al$_2$O$_3$ and 42.7% SiO$_2$.

The BET surface area is 278 m$^2$/g.

The total pore volume, measured by nitrogen adsorption, is 0.455 ml/g.

The mean pore diameter, measured by mercury porosimetry, is 64 Å.

The ratio between volume V2, measured by mercury porosimetry, encompassed between $D_{mean}$−30 Å and $D_{mean}$+30 Å, to the total mercury volume is 0.87.

Volume V3, measured by mercury porosimetry, encompassed in the pores with a diameter of more than $D_{mean}$+30 Å, is 0.03 ml/g.

Volume V6, measured by mercury porosimetry, encompassed in the pores with a diameter of more than $D_{mean}$+15 Å, is 0.037 ml/g.

The ratio between the adsorption surface area and the BET surface area is 0.80.

A pore volume, measured by mercury porosimetry, encompassed in the pores with a diameter of more than 140 Å is 0.011 ml/g.

The pore volume, measured by mercury porosimetry, encompassed in the pores with a diameter of more than 160 Å is 0.007 ml/g.

The pore volume, measured by mercury porosimetry, encompassed in the pores with a diameter of more than 200 Å is 0.005 ml/g.

The pore volume, measured by mercury porosimetry, encompassed in the pores with a diameter of more than 500 Å is 0.001 ml/g.

The B/L ratio of the substrate is 0.12.

The packing density of the catalyst is 1.07 g/cm$^3$.

The X diffraction diagram contains the main lines that are characteristic of the gamma-alumina, and in particular it contains the peaks at one d encompassed between 1.39 and 1.40 Å and the peaks at one d encompassed between 1.97 Å and 2.00 Å.

The atomic sodium content is 200+/−20 ppm. The atomic sulfur content is 800 ppm.

The NMR MAS spectra of the solid of $^{27}$Al of the catalysts show two clusters of separate peaks. A first type of aluminum whose maximum resonates toward 10 ppm extends between −100 and 20 ppm. The position of the maximum suggests that these radicals are essentially of $Al_{VI}$ type (octahedral). A second type of minority aluminum whose maximum resonates toward 60 ppm extends between 20 and 100 ppm. This cluster can be decomposed into at least two radicals. The predominant radical of this cluster would correspond to $Al_{IV}$ atoms (tetrahedral). The proportion of octahedral $Al_{VI}$ is 70%.

The catalyst contains a single silico-aluminum zone with an Si/Al ratio that is determined by TEM microprobe to be 0.65.

EXAMPLE 9

Preparation of Catalysts that can be Used in the Process According to the Invention (C1 to C8)

Catalyst C1 is obtained starting from the SA1 substrate in the form of extrudates. Catalysts C2, C3, C4, C5, C6, C7 and C8 are obtained by dry impregnation of an aqueous solution that contains platinum salts (chloroplatinic acid or tetramine platinum chloride) and/or fluorine salts (ammonium bifluoride NH$_4$HF$_2$) of, respectively, substrates SA2, SA3, SA4, SA5, SA6, SA7 and SA8, in the form of extrudates and whose preparations were described respectively in Examples 1, 2, 3, 4, 5, 6, 7 and 8. After maturation at ambient temperature in a water-saturated atmosphere, the impregnated extrudates are dried at 120° C. for one night, then calcined at 400° C. under dry air.

TABLE 1

Contents By Weight of F, Cl, Pt of Catalysts C1 to C8

|  | C1 | C2 | C3 | C4 | C5 | C6 | C7 | C8 |
|---|---|---|---|---|---|---|---|---|
| % SiO$_2$/Substrate | 49.88 | 47.7 | 30.5 | 33.5 | 40.3 | 43.62 | 39.3 | 42.7 |
| % Al$_2$O$_3$/Substrate | 50.12 | 52.3 | 69.5 | 66.5 | 59.7 | 56.38 | 60.7 | 57.3 |
| F (% by Weight)/Catalyst | 0 | 1.6 | 0 | 1.5 | 0 | 1.5 | 3.1 | 4.8 |
| Cl (% by Weight) | 0 | 0 | 0 | 0 | 0.81 | 0.82 | 0.79 | 0.80 |
| Pt (% by Weight) | 0 | 0 | 0.3 | 0.3 | 0.3 | 0.3 | 0.3 | 0.3 |

EXAMPLE 10

Evaluation of the C1 to C8 Catalysts in Terms of Alkylation of Benzene

A catalytic reactor that comprises a reaction zone that contains 50 cm³ of prepared catalyst according to Example 9 is used.

The operating conditions for the alkylation of the benzene by dodecene-1 are as follows:

temperature: 135° C.

pressure: 4 MPa

VVH=1 h⁻¹ (cm³ of benzene+dodecene-1 feedstock per cm³ of catalyst and per hour)

Benzene/dodecene-1 molar ratio 1:30

A feedstock that contains 72% by weight of benzene and 28% by weight of dodecene-1 is prepared. This feedstock is introduced at the inlet of the catalytic reactor where the alkylation reaction takes place.

The catalytic performance levels are recorded in the table by expressing the number of hours of operation with a conversion of >95% and the linearity of the formed alkylbenzenes.

TABLE 2

Catalytic Performance Levels of Catalysts C1 to C8 in Terms of Alkylation of Benzene

| | C1 | C2 | C3 | C4 | C5 | C6 | C7 | C8 |
|---|---|---|---|---|---|---|---|---|
| Number of Hours/Conversion >95% | 35 | 39 | 36 | 41 | 37 | 43 | 45 | 45 |
| Linearity of the Alkylbenzene (%) | 91.8 | 92.3 | 91.9 | 92.3 | 91.9 | 92.1 | 92.4 | 92.2 |

EXAMPLE 11

Preparation of a Catalyst C9 (Not in Accordance with the Invention)

Catalyst C9, not in accordance with the invention, is obtained by shaping a silica-alumina with a composition of 75% SiO2-25% Al2O3, prepared by the oil-drop method that is known to one skilled in the art. The catalyst contains neither fluorine nor metal.

EXAMPLE 12

Evaluation of the Catalyst C9 in Terms of Alkylation of Benzene

Catalyst C9 was evaluated in terms of alkylation of benzene according to the same operating conditions as those described in Example 10. Table 3 provides the performances that are obtained. In comparison with catalyst C3 that contains 2× less SiO2, catalyst C9 is less active, and the linearity of the alkylbenzenes is lower.

TABLE 3

Catalytic Performance Levels of Catalyst C9 in Terms of Alkylation of Benzene

| | C9 |
|---|---|
| Number of hours/Conversion > 95% | 34 |
| Linearity of Alkylbenzene (%) | 90.8 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 03/13.083, filed Nov. 5, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Process for the production of at least one compound that is selected from among the 2-, 3-, 4-, 5-, and 6-phenylalkanes by alkylation of an aromatic compound by means of at least one olefin that comprises at least 9 carbon atoms per molecule, characterized in that the process is conducted in the presence of a catalyst that comprises at least one non-zeolitic substrate with a silicated alumina base that contains an amount of more than 6% by weight and less than or equal to 50% by weight of silica (SiO2) and that exhibits the following characteristics:

a mean pore diameter, measured by mercury porosimetry, encompassed between 20 and 140 Å, a total pore volume, measured by mercury porosimetry, encompassed between 0.1 ml/g and 0.6 ml/g, a total pore volume, measured by nitrogen porosimetry, encompassed between 0.1 ml/g and 0.6 ml/g, a BET specific surface area encompassed between 100 and 500 m²/g, a packing density of more than 0.85, a pore volume, measured by mercury porosimetry, encompassed in the pores with a diameter of more than 140 Å, of less than 0.1 ml/g, a pore volume, measured by mercury porosimetry, encompassed in the pores with a diameter of more than 160 Å, of less than 0.1 ml/g, a pore volume, measured by mercury porosimetry, encompassed in the pores with a diameter of more than 200 Å, of less than 0.1 ml/g, a pore volume, measured by mercury porosimetry, encompassed in the pores with a diameter of more than 500 Å, of less than 0.1 ml/g, an X diffraction diagram that contains at least the main lines that are characteristic of at least one of the transition aluminas contained in the group that consists of the alpha, rho, chi, eta, gamma, kappa, theta and delta aluminas, whereby said process is carried out at a temperature of between 30 and 400° C., a pressure of between 0.1 and 10 MPa, an hourly volumetric flow rate of 0.50 to 200 h−1, and an aromatic compound/olefin molar ratio of between 1:1 and 50:1.

2. Process according to claim 1, wherein the aromatic compound is benzene.

3. Process according to one of claims 1 to 2, wherein the catalyst exhibits a pore distribution such that the ratio between volume V2, measured by mercury porosimetry, encompassed between $D_{mean}$−30 Å and $D_{mean}$+30 Å, to the total mercury volume is more than 0.6, such that volume V3, measured by mercury porosimetry, encompassed in the pores with a diameter of more than $D_{mean}$+30 Å, is less than 0.1 ml/g, and such that volume V6, measured by mercury porosimetry, encompassed in the pores with a diameter of more than $D_{mean}$+15 Å is less than 0.2 ml/g.

4. Process according to one of claims 1 to 3, wherein the catalyst contains at least one hydrogenating element that is selected from the group that is formed by the noble elements of group VIII and the elements of group VIB of the periodic table.

5. Process according to one of claims 1 to 4, wherein the catalyst comprises at least one noble element of group VIII that is selected from the group that is formed by platinum, palladium and ruthenium.

6. Process according to claim 5, wherein the catalyst comprises platinum and palladium.

7. Process according to one of claims 4 to 6, wherein the content by mass of metals of group VIII or group VIB in metallic form or in oxide form is encompassed between 0.005 and 5% by weight.

8. Process according to one of the preceding claims, wherein the catalyst comprises at least one halogenated element.

9. Process according to claim 8, wherein the halogenated element is chlorine or fluorine.

10. Process according to claim 9, wherein the halogenated element is fluorine.

11. Process according to one of claims 8 to 10, wherein the content by mass of halogenated catalyst element is encompassed between 0.5 and 10% by weight.

12. Process according to one of the preceding claims, wherein the catalyst exhibits a bed crushing value of more than 0.5 MPa.

13. Process according to one of the preceding claims, wherein the catalyst substrate exhibits an acidity that is measured by infrared tracking of the thermodesorption of the pyridine such that the B/L ratio (number of Bronsted sites/number of Lewis sites) of the substrate is encompassed between 0.05 and 1.

14. Process according to one of the preceding claims, wherein the catalyst substrate comprises a single silico-aluminum zone that has an Si/Al ratio that is equal to the overall Si/Al ratio that is determined by X fluorescence and is less than 2.3.

15. Process according to one of the preceding claims, wherein the catalyst comprises at least two silico-aluminum zones that have Si/Al ratios that are less than or greater than the overall Si/Al ratio determined by X fluorescence.

16. Process according to one of the preceding claims, wherein the reactions of alkylation and transalkylation take place in a joint reaction.

17. Process according to claim 16 that comprises the following successive stages in the combined alkylation and transalkylation zone:

Reaction of the aromatic compound with a feedstock that contains at least one olefin upon contact with the catalyst based on silicated alumina (alkylation reaction), fractionation of the product that is obtained so as to collect separately a first fraction that contains unconverted aromatic compound, a second fraction that contains at least one olefin that is initially present in the feedstock (unconverted), a third fraction that contains 2-, 3-, 4-, 5- and 6-phenylalkanes, and a fourth fraction that contains at least one poly-alkylaromatic compound (or poly-alkylaromatic fraction), whereby the latter is then at least partially recycled to said reaction zone where it reacts with the aromatic compound upon contact with the catalyst, so as to be at least partially transalkylated (transalkylation reaction), collection of a mixture of 2-, 3-, 4-, 5- and 6-phenylalkanes.

18. Process according to claim 17, wherein the first fraction that contains the unconverted aromatic compound is at least partially recycled to the joint reaction zone.

19. Process according to one of claims 17 to 18, wherein the second fraction that contains at least one unconverted olefin is at least partially recycled in the reaction zone.

20. Process according to one of claims 17 to 19, wherein the heavy alkylaromatic compounds are at least eliminated from the recycled portion of the fourth fraction by fractionation.

21. Process according to one of the preceding claims, wherein the alkylation reaction is carried out in the presence of hydrogen.

22. Process according to one of the preceding claims, wherein the olefinic feedstock consists for the most part of paraffins.

* * * * *